US008563749B2

(12) United States Patent
Siegel et al.

(10) Patent No.: US 8,563,749 B2
(45) Date of Patent: Oct. 22, 2013

(54) PROCESS FOR PREPARING SUBSTITUTED 1,3-DIHYDRO-2H-INDOL-2-ONES

(75) Inventors: Konrad Siegel, Düsseldorf (DE); Gunter Karig, Hofheim am Taunus (DE)

(73) Assignee: Bayer Cropscience AG, Monheim (DE)

( * ) Notice: Subject to any disclaimer, the term of this patent is extended or adjusted under 35 U.S.C. 154(b) by 73 days.

(21) Appl. No.: 13/103,673

(22) Filed: May 9, 2011

(65) Prior Publication Data

US 2011/0275832 A1    Nov. 10, 2011

Related U.S. Application Data

(60) Provisional application No. 61/332,949, filed on May 10, 2010.

(30) Foreign Application Priority Data

May 10, 2010  (EP) .................................... 10162381

(51) Int. Cl.
*C07D 209/34*    (2006.01)
(52) U.S. Cl.
USPC ....................................................... 548/486
(58) Field of Classification Search
USPC ....................................................... 548/486
See application file for complete search history.

(56) References Cited

U.S. PATENT DOCUMENTS 4,160,032 A   7/1979   Hardtmann
4,503,073 A   3/1985   Walsh et al.

OTHER PUBLICATIONS

J. Am Chem. Soc., vol. 95, No. 8, (1973), p. 2718-2719.
J. Med. Chem., vol. 25, (1982), p. 446-451.
Chem. Pharm. Bull., vol. 32, No. 5, (1984), p. 1995-1997.
Chem. Pharm. Bull., vol. 49, No. 9, (2001), p. 1132-1137.
Chem. Commun., (2007), p. 495-500.
Synlett, (1996), p. 663-664.

*Primary Examiner* — Shawquia Young
(74) *Attorney, Agent, or Firm* — Frommer Lawrence & Haug LLP

(57)    ABSTRACT

Process for preparing 1,3-dihydro-2H-indol-2-ones, starting from thioalkyl-, or thiocycloalkyl-substituted indol-2-one compounds, involving a) dissolving or suspending the thioalkyl-, or thiocycloalkyl-substituted indol-2-one compounds in a polar solvent,
b) adding a sulfur-containing salt to the solution or suspension, and
c) heating the reaction mixture under reflux at a temperature which corresponds at most to the boiling temperature of the solvent.

Use of the inventively prepared 1,3-dihydro-2H-indol-2-one as intermediates for the synthesis of fine chemicals and active ingredients from pharmacy and/or agriculture.

19 Claims, No Drawings

PROCESS FOR PREPARING SUBSTITUTED 1,3-DIHYDRO-2H-INDOL-2-ONES 1,3-Dihydro-2H-indol-2-ones of the formula (I)

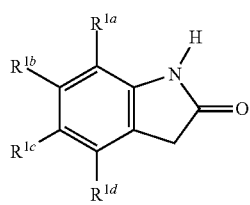

are intermediates for active ingredients used in the provision of pharmaceutical or crop-protection compositions.

Compounds of the formula (I) can be prepared, for example, by reduction from 3-(alkylsulfanyl)-1,3-dihydro-2H-indol-2-ones. The latter compounds are readily preparable on a laboratory scale. For their reduction, however, the only processes described to date are processes which are difficult to operate on an industrial scale. They are expensive and, furthermore, may also present safety challenges.

The prior art has already disclosed metal-catalyzed or metal salt-catalyzed processes for the conversion of thioalkyl-substituted indol-2-one compounds of the formula (II) into the 3-unsubstituted indole compounds of the formula (I). The compilation below of these known reduction methods, which, however, are suitable only for the laboratory scale, is a record of the fact that the development of suitable methods in this area is based on efforts which have already expended over a long period of time.

The reagents used in the prior-art processes listed below are indicated in parentheses in each case:

P. G. Grassmann, T. J van Bergen, Journal of the American Chemical Society 1973, pp. 2718-2719 (Raney nickel), U.S. Pat. No. 4,160,032, based on an application filed in 1974 (palladium and Raney nickel), D. A. Walsh, D. A. Shamblee, W. J. Welstead, L. F. Sancilio, J. Med. Chem. 1982, 25, 446-451 (Raney nickel), Y. Tamura, J. Uenishi, H. D. Choi, J. Haruta, H. Ishibashi, Chem. Pharm. Bull. 1984, 32, 1995-1997 (zinc powder in acetic acid), D. A. Walsh, D. A. Shamblee, U.S. Pat. No. 4,503,073 (tin in hydrochloric acid instead of Raney nickel), Y. Horiguchi, A. Sonobe, T. Saitoh, J. Toda, T. Sano, Chem. Pharm. Bull. 2001, 49, 1132-1137 ($NiCl_2$ and $NaBH_4$), and M. Miller, W. Tsang, A. Merritt, D. J. Procter, Chem. Commun. 2007, 498-500 ($SmI_2$).

For the same conversion, i.e., conversion of thioalkyl-substituted indol-2-one compounds of the formula (II) into the 3-unsubstituted indole compounds of the formula (I), T. J. Connolly and T. Durst, Synlett 1996, 663-664 disclose the further possibility of using $PPh_3$ in combination with p-TsOH as a reagent.

So the known processes utilize either a heavy metal reagent or triphenylphosphine. In the former case, wastes containing heavy metal are produced. For both environmental and economic reasons, this is not desirable. In the second case, the reaction product formed from the triphenylphosphine must be separated from the reaction mixture. This separation can be accomplished usually only by chromatography, with additional effort and expense.

Moreover, the respective reagent has a high molar mass and nevertheless must be used stoichiometrically. This is a disadvantage on economic grounds.

The processes known from the prior art, however, are useful only on the laboratory scale, and, on account of the chemical properties of the metal compounds used as reagents, also have disadvantages, the disadvantages having even greater consequences when the processes are employed on an operational scale.

Against this background, the object of the invention lies in the development of a process that allows the compound of the formula (I) to be prepared on an operational scale and that does not exhibit the disadvantages of the processes known from the prior art.

The object is achieved by means of a single-stage process for preparing a compound of the formula (I)

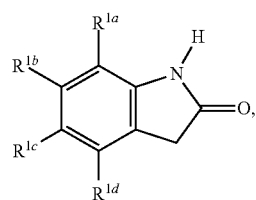

in which $R^{1a}$ to $R^{1d}$ independently of one another are selected from the group consisting of hydrogen, fluorine, chlorine, bromine, and trifluoromethyl, ($C_1$-$C_6$)-alkyl, the alkyl radical being unsubstituted or being substituted by one or more substituents selected from the group consisting of ($C_1$-$C_4$)-alkoxy or ($C_3$-$C_7$)-cycloalkyl, ($C_3$-$C_7$)-cycloalkyl, the cycloalkyl radical being unsubstituted or being substituted by one or more substituents selected from the group consisting of ($C_1$-$C_4$)-alkyl or ($C_3$-$C_7$)-cycloalkyl or ($C_1$-$C_4$)-alkoxy, ($C_1$-$C_6$)-alkoxy, the alkoxy radical being branched or unbranched and being unsubstituted or substituted by one or more substituents selected from the group consisting of ($C_1$-$C_4$)-alkoxy or ($C_3$-$C_7$)-cycloalkyl, ($C_3$-$C_7$)-cycloalkoxy, the cycloalkoxy radical being unsubstituted or being substituted by one or more substituents selected from the group consisting of ($C_1$-$C_4$)-alkyl or ($C_1$-$C_4$)-alkoxy, ($C_1$-$C_6$)-alkylthio, the alkylthio radical being branched or unbranched and being unsubstituted or substituted by one or more substituents selected from the group consisting of ($C_1$-$C_4$)-alkyl or ($C_1$-$C_4$)-alkoxy, ($C_3$-$C_7$)-cycloalkylthio, the cycloalkylthio radical being unsubstituted or being substituted by one or more substituents selected from the group consisting of ($C_1$-$C_4$)-alkyl or ($C_1$-$C_4$)-alkoxy, and phenyl or 1-naphthyl or 2-baphthyl or a five- or six-membered heteroaromatic ring having 1 to 2 heteroatoms, the heteroatoms being selected independently of one another from the group consisting of O or N, and the aryl or heteroaryl radical being unsubstituted or being substituted by one or more substituents selected from the group consisting of $(C_1-C_4)$-alkyl, $(C_1-C_4)$-alkoxy or $(C_3-C_7)$-cycloalkyl or $(C_1-C_4)$-alkylthio, starting from a compound of formula (II)

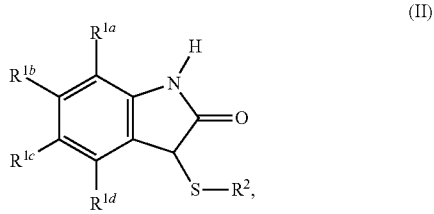

(II)

in which $R^{1a}$ to $R^{1d}$ are defined as in formula (I), and $R^2$ is an unsubstituted or substituted $(C_1-C_{14})$-alkyl, $(C_3-C_7)$-cycloalkyl, benzyl or a $CH_2-C(O)O-(C_1-C_6)$-alkyl, which comprises a) dissolving or suspending a compound of formula (II) in a polar solvent, b) adding a sulfur-containing salt to the solution or suspension, and c) heating the reaction mixture under reflux at a temperature which corresponds at most to the boiling temperature of the polar solvent.

The process of the invention allows simple, safe, and cost-effective preparation of compounds of the formula (I) from compounds of the formula (II).

The process can be carried out safely even on the operational scale. Advantageously, moreover, the process can be flexibly tailored to the existing apparatus.

A particularly surprising and very advantageous feature is that the process of the invention does not produce intensely odored waste gases of the kind which really are to be expected from such a reaction. A presumed basis for this advantage is that the sulfur-containing leaving group is bound in a non-volatile form.

Preferred phenyl substituents $R^{1a}$, $R^{1b}$, $R^{1c}$, and $R^{1d}$ are radicals selected independently of one another from the group consisting of hydrogen, $(C_1-C_6)$-alkyl, $(C_1-C_6)$-alkoxy, fluorine, chlorine, bromine, and trifluoromethyl.

Particularly preferred phenyl substituents $R^{1a}$, $R^{1b}$, $R^{1c}$ and $R^{1c}$ are radicals selected independently of one another from the group consisting of hydrogen, methoxy, fluorine, and chlorine.

Preferred for the radical $R^2$ is unsubstituted or substituted $(C_1-C_6)$-alkyl, $(C_3-C_7)$-cycloalkyl, benzyl or $CH_2-C(O)O-(C_1-C_6)$-alkyl, the substituents being selected independently of one another from the group consisting of hydrogen, $(C_1-C_6)$-alkyl or $(C_3-C_7)$-cycloalkyl.

A preferred polar solvent is water, a $(C_1-C_4)$ alcohol or a mixture of water and a $(C_1-C_4)$ alcohol. In this context, it is possible to employ, inter alia, a mixture of water and a polar solvent which is stable under the reaction conditions but is other than a $(C_1-C_4)$ alcohol. The polar solvent wholly or at least partly dissolves the sulfur-containing salt that acts as a reducing agent.

In a further preferred embodiment, the sulfur-containing salt is selected from the group consisting of alkali metal or alkaline earth metal sulfite, alkali metal or alkaline earth metal bisulfite, alkali metal or alkaline earth metal thionite, alkali metal or alkaline earth metal dithionite or alkali metal or alkaline earth metal thiosulfate.

Especially preferred as sulfur-containing salts are the respective sodium salts, i.e., the sulfur-containing salt is selected from the group consisting of sodium bisulfite, sodium sulfite, sodium thionite, sodium dithionite, and sodium thiosulfate.

The sulfur-containing salts that are most preferred are sodium bisulfite or sodium sulfite, and a mixture of both can also be used.

If sodium bisulfite is used as a sulfur-containing salt, water is the preferred polar solvent, since this combination of reagent and solvent leads to very high yields.

It is preferred to add from 2 to 3 equivalents of the sulfur-containing salt to the reaction mixture.

It is particularly preferred to add from 2 to 2.5 equivalents of the sulfur-containing salt to the reaction mixture.

A further preferred embodiment envisages the reaction mixture being heated to a temperature which lies within a range whose lower limit is 40° C. and whose upper limit corresponds to the reflux temperature of the solvent.

Particularly preferred, however, is the version of the process at a reaction temperature which corresponds approximately to the boiling temperature of the solvent respectively used. In this case the reaction may also be carried out under elevated pressure, in order to attain a temperature which lies up to 15° C. above the boiling point of the respective solvent under atmospheric pressure. A reaction temperature increased by up to 15° C. makes it possible, advantageously, for the reaction time to be shortened.

In one preferred embodiment the heating of the reaction mixture takes place with stirring for a duration of 1 to 48 hours.

Particularly preferred is the heating of the reaction mixture with stirring for a duration of 1 to 24 hours, and a reaction time of 2 to 12 hours is most preferred.

It is within the scope of the invention to add a defoamer or a mixture of different defoamers to the reaction mixture before the boiling temperature of the solvent respectively used has been reached. Examples of suitable defoamers include Fluowet PL 80 and Korasilon LP-Si E 1051.

The defoamer preferably is added before the beginning of the heating of the reaction mixture. It is likewise within the scope of the invention for, prior to the isolation of the reaction product, a precipitant to be added to the reaction mixture, the precipitant being selected from the group of polar solvents consisting of water, a $(C_1-C_4)$ alcohol or a mixture of water and a $(C_1-C_4)$ alcohol. The addition of the precipitant has the advantage, in particular, that the yield is increased on isolation by filtration.

Alternatively to isolation by filtration, the reaction product of formula (I) may also be used further without isolation, in the form, for example, of a suspension or solution, in the synthesis of fine chemicals and active ingredients in pharmacy and/or agriculture.

A further aspect of the invention, accordingly, concerns the use of a compound of the formula (I) for preparing fine chemicals and active ingredients with pharmaceutical or herbicidal activity.

Furthermore the use of a compound of the formula (I) for preparing ingredients with insecticidal or fungicidal activity is within the scope of the invention.

The examples below elucidate the invention in more detail, but without confining its subject matter to these examples.

EXAMPLES

Example 1

Preparation of 7-fluoro-1,3-dihydro-2H-indol-2-one

7-Fluoro-3-(methylsulfanyl)-1,3-dihydro-2H-indol-2-one (270.5 g) was dissolved in water (2000 g) and admixed with sodium bisulfite (300 g). The mixture was heated to reflux, in the course of which it was vigorously stirred. After 2.25 h, the mixture was cooled to 25° C. and isolated by filtration on a suction filter. It was washed twice with water (500 g each time) and then dried under reduced pressure (<50 mbar, 50° C.). This gave 7-fluoro-1,3-dihydro-2H-indol-2-one as a white solid (206.3 g, 95.1% by weight, 95% yield).

LC-MS: M+H=152 (100%).

$^1$H-NMR (400 MHz, CDCl$_3$): δ (ppm)=3.59 (s, 2H), 6.94-7.04 (m, 3H), 8.22 (s, broad, H).

Example 2

Preparation of 5-fluoro-1,3-dihydro-2H-indol-2-one

5-Fluoro-3-(methylsulfanyl)-1,3-dihydro-2H-indol-2-one (20 g) was reacted in the same way as in Example 1. This gave 5-fluoro-1,3-dihydro-2H-indol-2-one as a solid (13.5 g, 93% yield).

LC-MS: M+H=152 (100%).

$^1$H-NMR (400 MHz, CDCl$_3$): δ (ppm)=3.55 (s, 2H), 6.78 (dd, I H), 6.89-7.00 (m, 2H), 8.32 (s, broad, H).

Example 3

Preparation of 7-chloro-1,3-dihydro-2H-indol-2-one

7-Chloro-3-(methylsulfanyl)-1,3-dihydro-2H-indol-2-one (20 g) was reacted in the same way as in Example 1. This gave 7-chloro-1,3-dihydro-2H-indol-2-one as a solid (15.6 g, 99% yield).

LC-MS: M+H=168 (100%), 170 (60%).

$^1$H-NMR (400 MHz, CDCl$_3$): δ (ppm)=3.62 (s, 2H), 6.96 (t, 1H), 7.13 (d, I H), 7.22 (d, IH), 8.17 (s, broad, H).

Example 4

Preparation of 5,7-difluoro-1,3-dihydro-2H-indol-2-one 5,7-Difluoro-3-(methylsulfanyl)-1,3-dihydro-2H-indol-2-one (4.25 g) was reacted in the same way as in Example 1. This gave the title compound as a solid (3.04 g, 91% yield).

LC-MS: M+H=170 (100%).

$^1$H-NMR (400 MHz, CDCl$_3$): δ (ppm)=3.58 (s, 2H), 6.76-6.84 (m, 2H), 7.91 (s, broad, 1H).

Example 5

Preparation of 7-methoxy-1,3-dihydro-2H-indol-2-one

7-Methoxy-3-(methylsulfanyl)-1,3-dihydro-2H-indol-2-one (1.86 g) was reacted in the same way as in Example 1. This gave the title compound as a solid (1.43 g, 95% yield).

LC-MS: M+H=164

$^1$H-NMR (400 MHz, CDCl$_3$): δ (ppm)=3.55 (s, 2H), 3.87 (s, 3H), 6.83 (dd, 2H), 6.98 (t, 1H), 7.83 (s, broad, 1H).

What is claimed is:

1. A process for preparing a compound of formula (I):

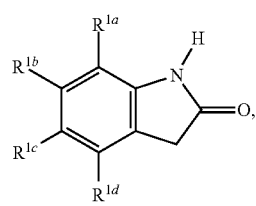

in which
  $R^{1a}$ to $R^{1d}$ independently of one another are selected from the group consisting of:
    hydrogen, fluorine, chlorine, bromine, and trifluoromethyl;
    ($C_1$-$C_6$)-alkyl, the alkyl radical being unsubstituted or being substituted by one or more substituents selected from the group consisting of ($C_1$-$C_4$)-alkoxy and ($C_3$-$C_7$)-cycloalkyl;
    ($C_3$-$C_7$)-cycloalkyl, the cycloalkyl radical being unsubstituted or being substituted by one or more substituents selected from the group consisting of ($C_1$-$C_4$)-alkyl, ($C_3$-$C_7$)-cycloalkyl, and ($C_1$-$C_4$)-alkoxy;
    ($C_1$-$C_6$)-alkoxy, the alkoxy radical being branched or unbranched and being unsubstituted or substituted by one or more substituents selected from the group consisting of ($C_1$-$C_4$)-alkoxy and ($C_3$-$C_7$)-cycloalkyl;
    ($C_3$-$C_7$)-cycloalkoxy, the cycloalkoxy radical being unsubstituted or being substituted by one or more substituents selected from the group consisting of ($C_1$-$C_4$)-alkyl and ($C_1$-$C_4$)-alkoxy;
    ($C_1$-$C_6$)-alkylthio, the alkylthio radical being branched or unbranched and being unsubstituted or substituted by one or more substituents selected from the group consisting of ($C_1$-$C_4$)-alkyl and ($C_1$-$C_4$)-alkoxy;
    ($C_3$-$C_7$)-cycloalkylthio, the cycloalkylthio radical being unsubstituted or being substituted by one or more substituents selected from the group consisting of ($C_1$-$C_4$)-alkyl and ($C_1$-$C_4$)-alkoxy; and
    phenyl or 1-naphthyl or 2-naphthyl or a five- or six-membered heteroaromatic ring having 1 to 2 heteroatoms, the heteroatoms being selected independently of one another from the group consisting of O or N, and the aryl or heteroaryl radical being unsubstituted or being substituted by one or more substituents selected from the group consisting of ($C_1$-$C_4$)-alkyl, ($C_1$-$C_4$)-alkoxy, ($C_3$-$C_7$)-cycloalkyl, and ($C_1$-$C_4$)-alkylthio;
starting from a compound of formula (II):

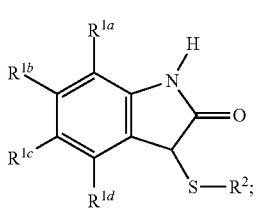

in which:

$R^{1a}$ to $R^{1d}$ are defined as in formula (I); and $R^2$ is an unsubstituted or substituted $(C_1-C_{14})$-alkyl, $(C_3-C_7)$-cycloalkyl, benzyl or a $CH_2-C(O)O-(C_1-C_6)$-alkyl;

which comprises:

a) dissolving or suspending a compound of the formula (II) in a polar solvent;

b) adding a sulfur-containing salt to the solution or suspension; and c) heating the reaction mixture under reflux at a temperature which corresponds at most to the boiling temperature of the polar solvent.

2. The process for preparing a compound of formula (I) as claimed in claim 1;

wherein $R^{1a}$ to $R^{1d}$ independently of one another are selected from the group consisting of hydrogen, $(C_1-C_6)$-alkyl, $(C_1-C_6)$-alkoxy, fluorine, chlorine, bromine, and trifluoromethyl.

3. The process for preparing a compound of formula (I) as claimed in claim 2;

wherein $R^{1a}$ to $R^{1d}$ independently of one another are selected from the group consisting of hydrogen, methoxy, fluorin, and chlorine.

4. The process for preparing a compound of formula (I) as claimed in claim 1;

wherein $R^2$ is an unsubstituted or substituted $(C_1-C_6)$-alkyl, $(C_3-C_7)$-cycloalkyl, benzyl, or $CH_2-C(O)O-(C_1-C_6)$-alkyl, the substituents being selected independently of one another from the group consisting of hydrogen, $(C_1-C_6)$-alkyl and $(C_3-C_7)$-cycloalkyl.

5. The process for preparing a compound of formula (I) as claimed in claim 1;

wherein the polar solvent is water, a $(C_1-C_4)$ alcohol, or a mixture of water and a $(C_1-C_4)$ alcohol.

6. The process for preparing a compound of formula (I) as claimed in claim 1;

wherein the sulfur-containing salt is an alkali metal or alkaline earth metal sulfite, alkali metal or alkaline earth metal bisulfate, alkali metal or alkaline earth metal thionite, alkali metal or alkaline earth metal dithionite, or alkali metal or alkaline earth metal thiosulfate.

7. The process for preparing a compound of formula (I) as claimed in claim 6;

wherein the sulfur-containing salt is selected from the group consisting of sodium bisulfate, sodium sulfite, sodium thionite, sodium dithionite, and sodium thiosulfate.

8. The process for preparing a compound of formula (I) as claimed in claim 7;

wherein the sulfur-containing salt is sodium sulfite, sodium bisulfite, or a mixture of both.

9. The process for preparing a compound of formula (I) as claimed in claim 6;

wherein 2 to 3 equivalents of the sulfur-containing salt are added to the reaction mixture.

10. The process for preparing a compound of formula (I) as claimed in claim 9;

wherein 2 to 2.5 equivalents of the sulfur-containing salt are added to the reaction mixture.

11. The process for preparing a compound of formula (I) as claimed in claim 1;

wherein the reaction mixture is heated to a temperature which lies between 40° C. and the reflux temperature of the respective solvent.

12. The process for preparing a compound of formula (I) as claimed in claim 11;

wherein the reaction temperature corresponds to the reflux temperature of the solvent respectively used.

13. The process for preparing a compound of formula (I) as claimed in claim 1;

wherein the heating of the reaction mixture takes place with stirring for a duration of 1 to 48 hours.

14. The process for preparing a compound of formula (I) as claimed in claim 13;

wherein the heating of the reaction mixture takes place with stirring for a duration of 1 to 24 hours.

15. The process for preparing a compound of formula (I) as claimed in claim 1;

wherein a defoamer or a mixture of different defoamers is added to the reaction mixture.

16. The process for preparing a compound of formula (I) as claimed in claim 1;

wherein, prior to isolation of the reaction product of the formula (I) by filtration, a precipitant is added to the reaction mixture, the precipitant being selected from the group of polar solvents consisting of water, a $(C_1-C_4)$ alcohol, and a mixture of water and a $(C_1-C_4)$ alcohol.

17. The process for preparing a compound of formula (I) as claimed in any one of the preceding claims;

wherein the reaction product is isolated by filtration after the reaction is completed.

18. A method of preparing chemicals and active ingredients with pharmaceutical or with herbicidal activity, comprising:

utilizing a compound of the formula (I):

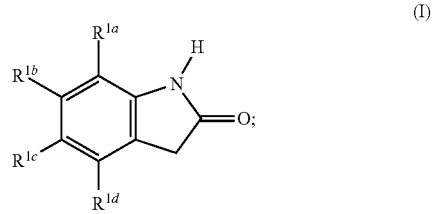

in which:

$R^{1a}$ $R^{1d}$ are as defined in claim 1, and prepared as claimed in claim 1.

19. The process for preparing a compound of formula (I) as claimed in claim 14;

wherein the heating of the reaction mixture takes place with stirring for a duration of 2 to 12 hours.

* * * * *